United States Patent [19]
Golovin

[11] Patent Number: 5,498,491
[45] Date of Patent: Mar. 12, 1996

[54] SOLID ELECTROLYTES DERIVED BY POLYMERIZATION OF VINYL SULFONATE DERIVATIVES

[76] Inventor: Milton N. Golovin, 145 Manton Dr., San Jose, Calif. 95123

[21] Appl. No.: 193,046

[22] PCT Filed: Jul. 22, 1993

[86] PCT No.: PCT/US93/06854

§ 371 Date: Feb. 4, 1994

§ 102(e) Date: Feb. 4, 1994

[87] PCT Pub. No.: WO94/02454

PCT Pub. Date: Feb. 3, 1994

[51] Int. Cl.⁶ ............................................... H01M 10/40
[52] U.S. Cl. ........................ 429/192; 528/391; 558/41; 558/55
[58] Field of Search ............... 429/192; 528/391, 528/421; 558/46, 51, 55

[56] References Cited

U.S. PATENT DOCUMENTS

| | | |
|---|---|---|
| 3,335,163 | 8/1967 | Tesoro et al. . |
| 4,079,084 | 3/1978 | Houghton . |
| 4,737,422 | 4/1988 | Knight et al. ........................ 429/192 |
| 4,830,939 | 5/1989 | Lee et al. ............................. 429/192 |
| 4,908,283 | 3/1990 | Takahashi et al. ................... 429/192 |
| 4,925,751 | 5/1990 | Shackle et al. ...................... 429/191 |
| 5,262,253 | 11/1993 | Golovin ............................. 429/192 |

FOREIGN PATENT DOCUMENTS

| | | |
|---|---|---|
| 312160 | 4/1989 | European Pat. Off. . |
| 411693 | 2/1991 | European Pat. Off. . |

OTHER PUBLICATIONS

Patent Abstracts of Japan, vol. 15, No. 515 (P-1293) Dec. 29, 1991, For JP. 3-223841 (Konica).

*Primary Examiner*—Stephen Kalafut

[57] ABSTRACT

This invention is directed to solid electrolytes containing a solid polymeric matrix derived from vinyl sulfonate polyalkylene oxides.

24 Claims, No Drawings

SOLID ELECTROLYTES DERIVED BY POLYMERIZATION OF VINYL SULFONATE DERIVATIVES

BACKGROUND OF THE INVENTION

1. Field of the Invention

This invention is directed to novel vinyl sulfonate derivatives as well as to solid electrolytes derived by polymerization of such vinyl sulfonate derivatives.

2. State of the Art

Electrolytic cells comprising an anode, a cathode and a solid, solvent-containing electrolyte are known in the art and are usually referred to as "solid cells" or "solid batteries". These cells offer a number of advantages over electrolytic cells containing a liquid electrolyte (i.e., "liquid cells" or "liquid batteries") including improved safety features.

The solid, solvent-containing electrolyte employed in such solid batteries contains either an inorganic matrix or an organic polymeric matrix as well as a suitable inorganic ion salt. Because of their expense and difficulty in forming into a variety of shapes, inorganic non-polymeric matrices are, however, not preferred, and the art typically employs a solid electrolyte containing an organic or inorganic polymeric matrix.

Suitable organic polymeric matrices are well known in the art and are typically organic homopolymers obtained by polymerization of a suitable organic monomer as described, for example, in U.S. Pat. No. 4,908,283 or copolymers obtained by polymerization of a mixture of organic monomers. Suitable organic monomers include, by way of example, ethylene oxide, propylene oxide, ethyleneimine, epichlorohydrin, ethylene succinate, urethane acrylate, and an acryloyl-derivatized polyalkylene oxide containing an acryloyl group of the formula $CH_2=CR'C(O))-$ where R' is hydrogen or lower alkyl of from 1–6 carbon atoms.

One problem associated with the polymerization of certain organic monomers is that rather strong conditions are required to effect the desired degree of polymerization. The strong conditions used can have an adverse effect on the partially manufactured battery components treated under these conditions. Accordingly, the art has been searching for organic monomers which are readily polymerized and which, when polymerized, form suitable solid polymeric matrices for use in preparing solid electrolytes.

Additionally, suitable organic monomers preferably contain at least one hetero atom capable of forming donor acceptor bonds with inorganic cations (e.g., alkali ions). When polymerized, these compounds form a polymer suitable for use in an ionically conductive matrix in a solid electrolyte.

SUMMARY OF THE INVENTION

This invention is directed, in part, to the discovery of novel vinyl sulfonate derivatives (i.e., monomers) which are readily polymerized, and, when polymerized, the resulting polymer forms an ionically conductive solid matrix. The organic monomers of this invention are selected from the group consisting of the compounds set forth in formulas A, B, C, D and E below:

i

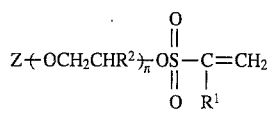

where $R^1$ is selected from the group consisting of hydrogen and alkyl of from 1 to 6 carbon atoms; $R^2$ is selected from the group consisting of hydrogen and an alkyl group of from 1 to 3 carbon atoms; Z is selected from the group consisting of a hydrocarbyl group of from 1 to 30 carbon atoms and a compatible ethylenically unsaturated moiety of from 2 to 6 carbon atoms; and n is an integer from about 2 to 50;

ii

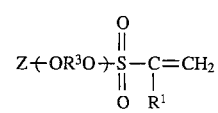

wherein $R^3$ is an alkylene group of from 2 to 10 carbon atoms, $R^1$ is selected from the group consisting of hydrogen and alkyl of from 1 to 6 carbon atoms; and Z is selected from the group consisting of a hydrocarbyl group of from 1 to 30 carbon atoms and a compatible ethylenically unsaturated moiety of from 2 to 6 carbon atoms;

iii $$\begin{array}{c} CH_2-R^4 \\ | \\ CH-R^4 \\ | \\ CH_2-R^4 \end{array} \qquad C$$

wherein each $R^4$ is independently selected from the group consisting of $-(OCH_2CHR^2)-_mOZ'$ where $R^2$ is hydrogen or an alkyl group of from 1 to 3 carbon atoms, Z' is a compatible ethylenic unsaturated moiety of from 2 to 6 carbon atoms, and m is an integer from 0 to 50;

with the proviso that at least one Z' is $$\begin{array}{c} O \\ \| \\ -OS-C=CH_2 \\ \| \; | \\ O \; R^1 \end{array}$$

wherein $R^1$ is selected from the group consisting of hydrogen and alkyl of from 1 to 6 carbon atoms;

iv $$\begin{array}{c} R^5CH_2 \diagdown \quad \diagup CH_2R^5 \\ C \\ \diagup \quad \diagdown \\ R^5CH_2 \quad CH_2R^6 \end{array} \qquad D$$

wherein each $R^5$ is independently selected from the group consisting of $-(OCH_2CHR^2)-_mOZ'$ where $R^2$ is hydrogen or an alkyl group of from 1 to 3 carbon atoms, Z' is a compatible ethylenic unsaturated moiety of from 2 to 6 carbon atoms, and m is an integer from 0 to 50, and $R^6$ is selected from the group consisting of hydrogen, alkyl of from 1 to 3 carbon atoms, and $-(OCH_2CHR^2)-_mOZ'$ where $R^2$, Z' and m are as defined above with the proviso that at least one Z' is

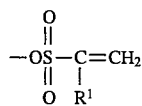

wherein R¹ is selected from the group consisting of hydrogen and alkyl of from 1 to 6 carbon atoms; and v

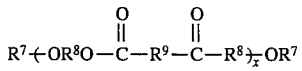

wherein x is an integer from 1 to about 50; each $R^8$ and $R^9$ is independently an alkylene group of from 2 to 10 carbon atoms; each $R^7$ is independently selected from the group consisting of a hydrocarbyl group of from 1 to 30 carbon atoms and $—(CH_2CHR^2O)—_mZ'$ where $r^2$ is selected from the group consisting of hydrogen and alkyl of from 1 to 3 carbon atoms, m is an integer from 0 to 50, and Z' is a compatible ethylenic unsaturated moiety of from 2 to 6 carbon atoms, with the proviso that at least one of $R^7$ is:

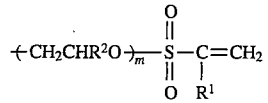

wherein R¹ is selected from the group consisting of hydrogen and alkyl of from 1 to 6 carbon atoms; and $R^2$ and m are as defined above.

When polymerized, these compounds form a polymer suitable for use as an ionically conductive matrix in a solid electrolyte. Accordingly, in another of its composition aspects, this invention is directed to a single-phase, solid, solvent-containing electrolyte which comprises:
 a solid polymeric matrix;
 an inorganic ion salt; and
 an electrolyte solvent;
wherein said solid polymeric matrix is obtained by polymerizing an organic monomer selected from the group consisting of the compounds set forth in formulas A, B, C, D, and E above.

In another of its composition aspects, the present invention is directed to an electrolytic cell which comprises:
 an anode comprising a compatible anodic material;
 a cathode comprising a compatible cathodic material; and
 interposed therebetween a single-phase, solid, solvent-containing electrolyte which comprises: a solid polymeric matrix;
 an inorganic ion salt; and
 an electrolyte solvent;
 wherein said solid polymeric matrix is obtained by polymerizing an organic monomer selected from the group consisting of the compounds set forth in formulas A, B, C, D, and E above.

In formulas A and B, Z is preferably:

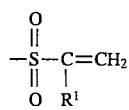

where R¹ is as defined above.

In formulas C and D, each of $R^4$ and $R^5$ is preferably

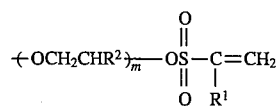

where R¹, R², and m are as defined above.
In formula D, $R^6$ is preferably hydrogen or

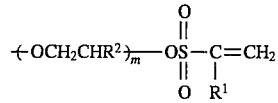

where R¹, R², and m are as defined above.
In formula E, each of $R^7$ is preferably

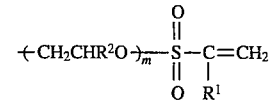

where r¹, R², and m are as defined above.

In formulas A–E, R¹ is preferably hydrogen or methyl and more preferably hydrogen; $R^2$ is preferably hydrogen or methyl and more preferably hydrogen; m is preferably an integer from 0 to about 30 and more preferably from 3 to about 20; and n is preferably an integer from 3 to about 30 and more preferably from 3 to about 20.

DETAILED DESCRIPTION OF THE PREFERRED EMBODIMENTS

As noted above, this invention is directed to solid, solvent-containing electrolytes which employ a specific solid, polymeric, ion-conducting matrix. However, prior to describing this invention in further detail, the following terms will first be defined.

Definitions

As used herein, the following terms have the following meanings.

The term "solid polymeric matrix" or "solid matrix" refers to an ion-conductive, electrolyte compatible material formed by polymerizing an organic monomer (or partial polymer thereof) which monomers are defined by formulas A–E above and which, when used in combination with the other components of the electrolyte, renders the electrolyte solid. Such matrices contain at least one hetero atom capable of forming donor acceptor bonds with inorganic cations derived from inorganic ion salts. The formation of solid polymeric matrices is well known in the art and is described, for example, in U.S. Pat. No. 4,908,283 and in U.S. Pat. No. 4,925,751 both of which are incorporated herein by reference in their entirety.

The term "a partial polymer of a monomer of formulas A–E" refers to monomers which have been partially polymerized to form reactive oligomers. Partial polymerization may be conducted for the purpose of enhancing the viscosity of the monomer, decreasing the volatility of the monomer, and the like. Partial polymerization is generally permitted so long as the resulting partial polymer can be further polymerized, preferably in the presence of the inorganic ion salt and the electrolyte solvent, to form a solid polymeric matrix which is suitable for use as solid electrolytes in electrolytic cells.

The term "inorganic ion salt" refers to any inorganic salt which is suitable for use in a solid electrolyte. The particular inorganic ion salt employed is not critical, and examples of suitable inorganic ion salts include $LiClO_4$, LiI, LiSCN, $LiBF_4$, $LiAsF_6$, $LiCF_3SO_3$, $LiPF_6$, NaI, NaSCN, KI, CsSCN, $AgNO_3$, $CuCl_2$, $Mg(ClO_4)_2$, $LiN(SO_2CF_3)_2$, $LiC(SO_2CF_3)_3$ and the like The inorganic ion salt preferably contains at least one atom selected from the group consisting of Li, Na, K, Cs, Ag, Cu and Mg.

The term "electrolyte solvent" refers to the solvent (i.e., plasticizer) added to the electrolyte and/or the cathode for the purpose of solubilizing the inorganic ion salt. The solvent can be any low volatile aprotic polar solvent. Preferably, these materials are characterized by a boiling point greater than about 85° C. In this regard, low volatility for the electrolyte solvent simplifies manufacture of the electrolyte/ batteries and improves their shelf life.

If the solid polymeric matrix is formed by radiation polymerization of a monomer of formulas A, B, C, D, or E above, then the electrolyte solvent should be radiation inert at least up to the levels of radiation employed. If the solid polymeric matrix is formed by thermal polymerization of such monomers, the electrolyte solvent should be thermally inert at least up to the temperatures of thermal polymerization. Additionally, the electrolyte solvent should not scavenge free radicals.

Representative examples of suitable electrolyte solvents include propylene carbonate, ethylene carbonate, γ-butyrolactone, tetrahydrofuran, glyme (dimethoxyethane), diglyme, triglyme, tetraglyme, dimethylsulfoxide, dioxolane, sulfolane and the like. A particularly preferred electrolyte solvent is a mixture of propylene or ethylene carbonate and triglyme (e.g., a 4:1 weight ratio of propylene carbonate and triglyme) as disclosed in U.S. Patent application Ser. No. 07/918,509 filed Jul. 22, 1992, which application is incorporated herein by reference in its entirety. More preferably, the mixture of propylene or ethylene carbonate and triglyme is employed in combination with $LiPF_6$ as disclosed in U.S. Patent application Ser. No. 08/049,212, filed Apr. 19, 1993, which application is incorporated herein by reference in its entirety.

The term "cured" or "cured product" refers to the treatment of a monomer of formulas A, B, C, D or E above (or partial polymer thereof) under polymerization conditions so as to form a solid polymeric matrix. The resulting cured product can include cross-linking between polymer backbones.

Suitable polymerization conditions are well known in the art and include, by way of example, heating the monomer, irradiating the monomer with UV light, electron beams, etc. Because the resulting solid polymeric matrix (i.e., cured product) contains repeating units having at least one oxygen (hetero) atom, the matrix is capable of forming donor acceptor bonds with inorganic cations (alkali ions) and is, accordingly, ion-conducting.

The monomers depicted in formulas A, B, C, D or E above (or the partial polymer thereof) can be cured (or further cured) prior to or after addition of the inorganic ion salt and the electrolyte solvent. For example, a composition comprising requisite amounts of a monomer of formulas A–E above (or mixtures thereof), the inorganic ion salt and the electrolyte solvent can be applied to a suitable substrate (e.g., the surface of the cathode) and then cured. Alternatively, a monomer of formulas A, B, C, D or E (or mixtures thereof) can be first cured and then dissolved into a suitable volatile solvent. Requisite amounts of the inorganic ion salt and electrolyte solvent can then be added to the solution containing the cured monomer (i.e., the solid polymeric matrix). The mixture is then placed on a substrate, and removal of the volatile solvent results in formation of a solid electrolyte.

In either case, the resulting solid electrolyte is a homogeneous, single-phase product which is maintained upon curing or evaporation, and does not readily separate upon cooling to temperatures below room temperature. Accordingly, the solid electrolyte of this invention does not include a separator as is typical of liquid electrolytes.

The term "hydrocarbyl" refers to organic radicals composed of carbon and hydrogen which may be aliphatic, alicyclic, aromatic or combinations thereof, e.g., aralkyl. Exemplary hydrocarbyl groups include alkyls such as methyl, ethyl, propyl, butyl, isobutyl, pentyl, hexyl, octyl, and the like, alkenyls such as propenyl, isobutenyl, hexenyl, octenyl, and the like, aromatics such as phenyl, alkylphenyls including 4-methylphenyl, 4-ethylphenyl, and the like, alkoxy such as ethoxyethyl, propoxyethyl, and the like.

The term "a compatible ethylenically unsaturated moiety of from 2 to about 6 carbon atoms" refers to unsaturated moieties on a compound of formulas A–E which either do not interfere with or which participate in the polymerization reaction to form a solid polymeric matrix. Suitable compatible ethylenically unsaturated moieties include, by way of example, $CH_2=CR'C(O)-$ where R' is hydrogen or alkyl of from 1 to 3 carbon atoms; a substituent of the formula

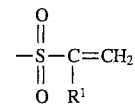

where $R^1$ is defined above; $CH_2=CH(CH_2)-_p$ where p is an integer from 1 to 5; and the like.

The term "solid electrolytic cell" refers to a composite containing an anode, a cathode, and a solid, ion-conducting electrolyte interposed therebetween. Preferably, the solid electrolytic cell is a secondary (rechargeable) electrolytic cell.

The anode is typically comprised of a compatible anodic material which is any material which functions as a negative pole (anode) in a solid electrolytic cell. Such compatible anodic materials are well known in the art and include, by way of example, lithium, lithium alloys, such as alloys of lithium with aluminum, mercury, zinc, and the like, and intercalation based anodes such as carbon, tungsten oxides, and the like.

The cathode comprises a compatible cathodic material which is any material which functions as a positive pole (cathode) in a solid electrolytic cell. Such compatible cathodic materials are well known in the art and include, by way of example, manganese dioxide, molybdenum trioxide, vanadium oxides such as $V_6O_{13}$, $LiV_3O_8$, $V_2O_5$, and the like, sulfides of titanium, molybdenum, niobium, and the like, chromium oxide, copper oxide, $LiCoO_2$, $LiMnO_2$, etc. The particular compatible cathodic material employed is not critical.

Preferably, the cathode is derived from a cathode paste comprising the compatible cathodic material and an electroconductive material including, by way of example, graphite, powdered carbon, powdered nickel, metal particles, conductive polymers (i.e., characterized by a conjugated network of double bonds like polypyrrole, polythiophene, polyaniline, and polyacetylene), and the like.

In a particularly preferred embodiment, the cathode is prepared from a cathode paste which comprises:

from about 35 to 65 weight percent of a compatible cathodic material;

from about 1 to 20 weight percent of an electroconductive material as described above;

from about 0 to 20 weight percent of a polyalkylene oxide film forming agent comprising repeating units of $$\left[ -CH_2CHO- \atop R \right]_x$$

where R is hydrogen or alkyl of from 1 to 3 carbon atoms and x is an integer such that the number average molecular weight of the film forming agent is at least about 100,000 and preferably from about 100,000 to about 5,000,000 and even more preferably from about 500,000 to about 750,000;

from about 10 to 50 weight percent of electrolytic solvent; and from at least about 5 weight percent to about 30 weight percent of a monomer of formulas A–E above (or partial polymer thereof)

wherein all weight percents are based on the total weight of the cathode.

The cathode paste is typically spread onto a suitable support such as a current collector and then cured by conventional methods to provide for a solid positive cathodic plate. The cathode (excluding the support) generally has a thickness of about 20 to about 150 microns.

Current collectors are well known in the art, some of which are commercially available. A particularly preferred current collector for the cathode is a roughened nickel (electrolytically deposited nickel) on nickel current collector (available as CF18/NiT from Fukuda Metal Foil & Powder Company, Ltd., Kyoto, Japan). Another preferred current collector is aluminum foil to which an adhesive layer has been applied. Such adhesive layers are described in the examples below as well as in U.S. Patent application Ser. No. 07/968,155, filed on Oct. 29, 1992, now abandoned and which is incorporated herein by reference in its entirety.

The current collectors are preferably attached to the surface of the cathode not facing the electrolyte but can also be attached to the anode. When the current collector is attached to the cathode, the cathode is interposed between the electrolyte and the current collector.

In still another preferred embodiment, the electrolyte solvent and the cathode solvent are identical.

Methodology

Methods for preparing solid electrolytes are well known in the art. This invention, however, utilizes a particular monomer in the preparation of solid polymeric matrix used in the solid electrolytes which monomer is represented by formulas A, B, C, D and E above.

The monomers of formulas A–E above are readily prepared as shown in reaction (1) below. In this reaction scheme, compound R'—(OH)$_m$ refers to the appropriate starting material corresponding to final product depicted in formulas A, B, C, D and E. Reaction (1) proceeds as follows:

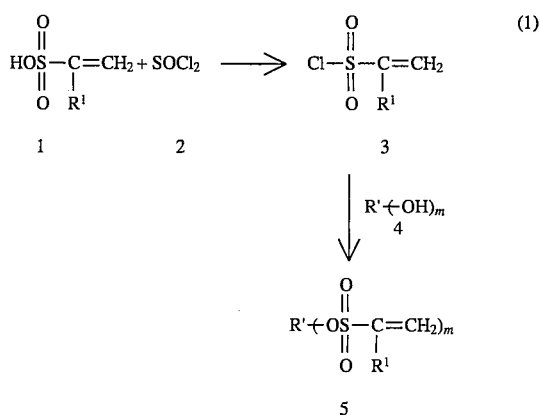

Specifically, in reaction (1), the vinyl-sulfonic acid (compound 1) is first converted to the acid chloride by contacting the acid with at least an equimolar amount and preferably an excess amount of thionyl chloride (compound 2). This reaction is conducted either neat or in an inert anhydrous solvent such as methylene chloride, chloroform, ethyl acetate, toluene, and the like. The reaction is generally conducted under an inert anhydrous atmosphere at from about 0° C. to about 30° C. The reaction is generally complete in about 0.5 to 3 hours.

The resulting acid chloride (compound 1) is then reacted with R'(OH)$_m$ (compound 4). In general, at least m moles and preferably about 1.1×m moles of acid chloride are used per mole of R'—(OH)$_m$ under conditions such that all of the hydroxyl groups on compound 4 are converted to

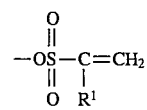

groups. Suitable reaction conditions include reaction temperatures of from about 0° C. to about 50° C. and reaction times of from 0.5 to 6 hours. The reaction is generally conducted in an inert, anhydrous solvent such as methylene chloride, dimethylformamide, ethyl acetate and the like. A tertiary amine such as triethylamine can be added to the solvent to scavenge the acid generated by the reaction, or, alternatively, a solvent such as pyridine can be employed. The product (compound 5) is then recovered by conventional techniques such as column chromatography, high performance liquid chromatography, distillation and the like. However, care should be taken during the recovery procedure (especially if distillation is employed) to prevent polymerization of the monomer.

The free acid (compound 1) is readily prepared from the acid salt by contacting with an aqueous acidic solution (e.g., 1N HCl). Some of the acid salts are commercially available (e.g., CH$_2$=CHSO$_3^-$Na$^+$), and others can be prepared by conventional procedures well known in the art. For example, the known BrCH$_2$CH(CH$_3$)SH compound (Journal of Organic Chemistry, Vol. 33, pp. 2895–2902 [1968]) can be converted to BrCH$_2$CH(CH$_3$)SO$_3$H by reaction first with Pb(NO$_3$)$_2$ and then with HNO$_3$ as per Cram & Hammond, "Organic Chemistry", p. 441, McGraw-Hill, New York, New York, U.S.A., (1959). Dehydrobromination under alkaline conditions (sodium methoxide/methanol) provides for the sodium salt of the CH$_2$=C(CH$_3$)SO$_3$H acid.

In reaction (1) above, the appropriate starting materials corresponding to the R'—(OH)$_m$ compound are either commercially available or can be prepared by methods well known in the art. Specifically, for compounds of formula A, the starting material is represented by the formula:

$$Z''\text{+}OCH_2CHR^2\text{)}_n\text{OH}$$

where Z" is either hydrogen, a hydrocarbyl group of from 1 to 30 carbon atoms, or an ethylenic unsaturated moiety. When Z" is hydrogen, the compounds are termed polyalkylene glycols, which compounds are commercially available (e.g., Aldrich) and/or can be prepared by standard polymerization processes.

When Z" is a hydrocarbyl group of from 1 to 30 carbon atoms, the appropriate starting materials can be prepared in the manner described in U.S. Pat. No. 4,728,451 which is incorporated herein by reference in its entirety.

When Z" is an ethylenic unsaturated moiety, one method for preparing these compounds is to initiate polymerization of an alkylene oxide (e.g., ethylene oxide) onto an ethylenic unsaturated alcohol (e.g., allyl alcohol, 3-buten-1-ol, and the like) in the manner described in U.S. Pat. No. 4,728,451. Suitable ethylenic unsaturated alcohols are commercially available. Another method for preparing these compounds is to react a polyalkylene glycol with an ethylenic unsaturated moiety containing carboxylic acid functionality (e.g., acrylic acid or its acid halide) to form the corresponding ester. In this reaction, the stoichiometry and the reaction conditions are controlled to provide for a preponderance of product wherein only some (e.g., one of two) of the hydroxyl groups are converted to esters containing such an ethylenic unsaturated moiety. Methods to form such esters are known per se to the skilled artisan as well as methods for their isolation and purification.

For compounds of formula B, the starting material is represented by the formula:

$$Z''\text{+}OR^3\text{)}\text{OH}$$

where Z" is either hydrogen, a hydrocarbyl group of from 1 to 30 carbon atoms, or an ethylenic unsaturated moiety. When Z" is hydrogen, the compounds are termed alkylene glycols, which compounds are commercially available (e.g., Aldrich). Compounds where Z" is a hydrocarbyl group of from 1 to 30 carbon atoms can be readily prepared by selective alkylation of the alkylene glycol. For example, reaction of the alkylene glycol with 1 equivalent of metallic sodium followed by addition of a hydrocarbyl chloride (e.g., an alkyl chloride) will result in the formation of hydrocarbyl—$OR^3$—OH which can then be separated from the resulting composition by conventional techniques (e.g., chromatography). When Z" is an ethylenic unsaturated moiety, these compounds are prepared in the manner described above for polyalkylene glycols.

The appropriate starting materials for the compounds of formula C are either commercially available (e.g., glycerol) or can be obtained by treating glycerol with an alkylene oxide in the manner described above as well as in U.S. Pat. No. 4,728,451. Control of the reaction conditions will lead to products having alkylene oxide substituents attached to one, two or all three of the hydroxyl groups of glycerol. Additionally, compounds such as $$\begin{array}{l}CH_2\text{+}OCH_2CH_2\text{)}_x\text{OH}\\ |\\ CH\text{+}OCH_2CH_2\text{)}_y\text{OH}\\ |\\ CH_2\text{+}OCH_2CH_2\text{)}_z\text{OH}\end{array}$$

where R is hydrogen, each $R^1$ is hydrogen and x+y+z is either 7 or 26 are commercially available from Lipo Chemicals Inc., Paterson, N.J., U.S.A. as Liponic EG-7 or Liponic EG-1, respectively.

The appropriate starting materials for certain of the compounds of formula D are either commercially available [e.g., pentaerythitol and 1,1,1-tris(hydroxymethyl)ethane] or are derived from such commercially available materials. For example, reaction of these with an alkylene oxide can be conducted in the manner described above. Control of the reaction conditions will lead to products having a polyalkylene oxide substituent attached to one or more of the hydroxyl groups.

The appropriate starting materials for the compounds of formula E are readily prepared by reacting an alkylene glycol of from 2 to 10 carbon atoms (e.g., ethylene glycol) with a difunctional carboxylic acid of from 2 to 10 carbon atoms (e.g., succinic acid) under conditions wherein a polymeric ester is formed. Such polymeric esters are represented by the formula:

$$HO\text{—}R^{11}\text{+}OC(O)\text{—}R^{12}\text{—}C(O)O\text{—}R^{11}\text{)}_x\text{OX}$$

where $R^{11}$, $R^{12}$ and x are as defined above. Use of a mixture of alkylene glycols and/or dicarboxylic acids under conditions known in the art will lead to different $R^{11}$ and $R^{12}$ groups within the formula. The resulting polymer can then be modified in the manner described above for the polyalkylene glycols to provide for the compounds of formula E.

The solid, solvent-containing electrolyte is then preferably prepared by combining a compound of formulas A–E or a mixture of such compounds with an inorganic ion salt and the electrolyte solvent. The resulting composition is then uniformly coated onto a suitable substrate (e.g., aluminum foil, a glass plate, a lithium anode, a cathode, etc.) by means of a roller, a doctor blade, a bar coater, a silk screen or spinner to obtain a film of this solution.

In order to enhance application of the electrolyte solution onto the substrate, this solution is preferably a liquid and even more preferably has a viscosity of from about 500 to about 10,000 centipoise at 25° C. and still more preferably has a viscosity of from about 1000 to about 4000 centipoise at 25° C. In some cases, it may be necessary to heat the solution so as to reduce the viscosity of the solution thereby providing for a coatable material.

Preferably, the amount of material coated onto the substrate is an amount sufficient so that after curing, the resulting solid, solvent-containing electrolyte has a thickness of no more than about 250 microns (μm). Preferably, the solid, solvent-containing electrolyte has a thickness of from about 15 to about 250 microns, more preferably from about 20 to about 150 microns, and even more preferably from about 25 to 80 microns.

The electrolyte solution typically comprises from about 5 to about 25 weight percent of an inorganic ion salt based on the total weight of the solution, and preferably from about 7 to 15 weight percent.

The electrolyte solution typically comprises from about 40 to about 80 weight percent electrolyte solvent based on the total weight of the electrolyte, preferably from about 60 to about 80 weight percent, and even more preferably from about 60 to 70 weight percent.

The electrolyte solution typically comprises from about 5 to about 30 weight percent of the polymer derived from a compound of formulas A–E above based on the total weight of the solution, preferably from about 10 to about 25 weight percent, and even more preferably from about 15 to 22 weight percent.

In a preferred embodiment, the electrolyte composition further comprises a small amount of a film forming agent. Suitable film forming agents are well known in the art and include, by way of example, polypropylene oxide, polyethylene oxide, copolymers thereof, and the like, having a numbered average molecular weight of at least about 100,000. Preferably, polyalkylene oxide film forming agent comprises repeating units of

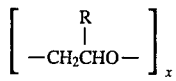

where R is hydrogen or alkyl of from 1 to 3 carbon atoms and x is an integer such that the number average molecular weight of the film forming agent is at least about 100,000 and preferably from about 100,000 to about 5,000,000 and even more preferably from about 500,000 to about 750,000. When employed, the film forming agent is employed in an amount of from about 1 to about 10 weight percent, more preferably from about 1 to 5 weight percent, and still more preferably from about 2.5 to 3.5 weight percent based on the total weight of the electrolyte solution.

Also, when the electrolyte solution employs a polyalkylene oxide film forming agent and $LiPF_6$ as the inorganic ion salt, it is preferably mixed in the manner described in Example 2 below as well as in U.S. Pat. No. 5,358,658, which patent is incorporated herein by reference in its entirety.

The resulting solution is then uniformly coated onto a suitable substrate (e.g., aluminum foil, a glass plate, a lithium anode, a cathode, etc.) by means of a roller, a doctor blade, a bar coater, a silk screen or spinner to obtain a film of this solution over the substrate.

In order to enhance its application of the electrolyte solution onto the substrate, this solution is preferably a liquid and even more preferably has a viscosity of from about 500 to about 10,000 centipoise at 25° C. and still more preferably has a viscosity of from about 1000 to about 4000 centipoise at 25° C. In some cases, it may be necessary to heat the solution so as to reduce the viscosity of the solution thereby providing for a coatable material.

Preferably, the amount of electrolyte solution coated onto the substrate is an amount sufficient so that after curing, the resulting solid, solvent-containing electrolyte has a thickness of no more than about 250 microns ($\mu m$). Preferably, the solid, solvent-containing electrolyte has a thickness of from about 25 to about 250 microns, more preferably from about 50 to about 150 microns, and even more preferably from about 50 to about 80 microns.

The composition is cured by conventional methods to form a solid film. For example, suitable curing methods include heating, irradiation with UV radiation, irradiation with electron beams (EB), etc. When the composition is cured by heating or UV radiation, the composition preferably contains an initiator. For example, when curing is by heating, the initiator is typically a peroxide such as benzoyl peroxide, methyl ethyl ketone peroxide, t-butyl peroxypyruvate, diisopropyl peroxycarbonate, and the like. When curing is by UV radiation, the initiator is typically benzophenone, Darocur 1173 (Ciba Geigy, Ardlesy, N.Y., U.S.A.), and the like.

The initiator is generally employed in an amount sufficient to catalyze the polymerization reaction. Preferably, the initiator is employed at up to about 1 weight percent based on the weight of the solid matrix forming monomer.

When curing is by EB treatment, an initiator is not required.

Without being limited to any theory, it is believed that the monomers of this invention provide for enhanced rates of polymerization as compared to other similar monomers (e.g., acryloyl-derivatized polyalkylene oxide) and, accordingly, provide for more facile polymerization because the electron withdrawing effects of the sulfonate substituent activate the ethylenic group to polymerization. In any event, the monomers of formulas A–E are readily polymerized under suitable polymerization conditions.

In an alternative embodiment, the solid polymeric matrix (e.g., formed by polymerization of a solid matrix forming monomer) can be dissolved into a suitable volatile solvent, and the requisite amounts of the inorganic ion salt and electrolyte solvent are then added. The mixture is then applied onto a suitable substrate (e.g., the surface of the cathode opposite the current collector) in the manner set forth above and the volatile solvent removed by conventional techniques (e.g., evaporation) to provide for a solid electrolyte. Suitable volatile solvents preferably have a boiling point of less than 85° C. and more preferably from about 45° C. to less than 85° C. Particularly preferred volatile solvents are aprotic solvents. Examples of suitable volatile solvents include acetonitrile, tetrahydrofuran and the like. However, acetonitrile is not preferred if it is to contact the anode.

In still another alternative embodiment, the liquid electrolyte solution is applied over a layer of cathode paste which itself is formed over a layer of electrically-conducting adhesion-promoter found on a metal foil. Both the cathode paste and the liquid electrolyte composition are simultaneously cured by exposure to, for example, electron beams so as to provide for a cured composite containing both the cured cathode and the cured electrolyte.

In any case, the resulting solid electrolyte is a homogeneous, single-phase material which is maintained upon curing and which does not readily separate upon cooling to temperatures below room temperature. See, for example, U.S. Pat. No. 4,925,751 which is incorporated herein by reference in its entirety.

Additionally, it may be desirable to avoid the use of any protic materials which will be incorporated into electrolyte of the electrolytic cell. If such removal is desired, then most of the protic inhibitors for preventing premature monomer polymerization employed with the monomers are preferably removed prior to formation of the solid matrix (e.g., the cathode and/or electrolyte) by contact with an inhibitor remover such as Inhibitor Remover available as product number 31,133–2 from Aldrich Chemical, Milwaukee, Wis., U.S.A. Such processes generally will lower the inhibitor concentration to less than about 50 ppm.

In a preferred embodiment, the process of forming an electrolytic cell comprises the steps of coating the surface of a cathode with a liquid composition comprising requisite amounts of a compound of formulas A–E or a mixture of compounds of formulas A–E, an inorganic ion salt and the electrolyte solvent. The composition is then cured to provide for a solid electrolyte on the cathodic surface. The anode (e.g., a lithium foil) is then laminated to this composite product in such a way that the solid electrolyte is interposed between the lithium foil and the cathodic material.

This process can be reversed so that the surface of an anode is coated with a composition comprising requisite amounts of a compound of formulas A–E or a mixture of compounds of formulas A–E, an inorganic ion salt and the electrolyte solvent. The composition is then cured to provide for a solid electrolyte on the anodic surface. The cathode is then laminated to this composite product in such a way that the solid electrolyte is interposed between the lithium foil and the cathodic material.

Methods for preparing solid electrolytes and electrolytic cells are also set forth in U.S. Pat. Nos. 4,830,939 and 4,925,751 which are incorporated herein by reference in their entirety.

The following examples are offered to illustrate the present invention and should not be construed in any way as limiting its scope.

EXAMPLES

EXAMPLE 1—Preparation of a Divinyl Sulfonate Derivative of Decaethylene Glycol

A divinyl sulfonate derivative of decaethylene glycol [H—(OCH$_2$CH$_2$)—$_{10}$OH] was prepared as follows:

Approximately, 100 g of vinyl sulfonate sodium salt (available from Aldrich Chemical Company, Milwaukee, Wis., U.S.A.) is converted to its free acid by addition to an aqueous solution of 1 N HCl. After stirring at room temperature for 1 hour, the free acid is then recovered by conventional means, e.g., extraction with ethyl acetate followed by drying with anhydrous magnesium sulfate.

The vinyl sulfonic acid is then converted to its acid chloride by reaction with approximately 1.1 equivalents of thionyl chloride at 10° C. with stirring for 30 minutes under a nitrogen atmosphere. The resulting product is then reacted with sufficient polyethylene glycol [HO—(CH$_2$CH$_2$O)—$_n$H—MW about 600 (n=~10) which is obtained from Aldrich Chemical Company, Milwaukee, Wis., U.S.A.] so as to provide approximately 1.1 equivalents of the vinyl sulfonic acid chloride per hydroxyl group. The reaction is conducted in ethyl acetate containing sufficient triethylamine to scavenge the acid generated. The reaction temperature is generally between about 10°–20° C., and the reaction is allowed to continue until complete (as determined by TLC). At this time, the reaction mixture is washed with water, aqueous sodium bicarbonate and water. The organic phase is then dried over anhydrous magnesium sulfate, filtered and the resulting product purified via column chromatography to provide for a vinyl sulfonate polyalkylene oxide of the formula:

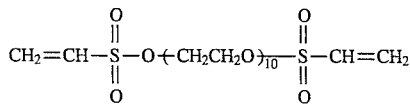

EXAMPLE 2—Preparation of a solid Electrolytic Cell Containing a Solid Electrolyte Having a Solid Polymeric Matrix Derived from the Vinyl Sulfonate Polyalkylene Oxide of Example 1

This example illustrates how a solid electrolytic cell containing a solid electrolyte prepared using a solid polymeric matrix derived from the compound of Example 1 could be prepared.

A solid electrolytic cell is prepared by first preparing a cathodic paste which is spread onto a current collector and is cured to provide for the cathode. An electrolyte solution is then placed onto the cathode surface and is cured to provide for the solid electrolyte composition. Then, the anode is laminated onto the solid electrolyte composition to provide for a solid electrolytic cell. The specifics of this construction are as follows:

A. The Current Collector

The current collector employed is a sheet of aluminum foil having a layer of adhesion promoter attached to the surface of the foil which will contact the cathode so as to form a composite having a sheet of aluminum foil, a cathode and a layer of adhesion promoter interposed therebetween.

Specifically, the adhesion promoter layer is prepared as a dispersed colloidal solution in one of two methods. The first preparation of this colloidal solution for this example is as follows:

84.4 parts by weight of carbon powder (Shawinigan Black™—available from Chevron Chemical Company, San Ramon, Calif., U.S.A.)

337.6 parts by weight of a 25 weight percent solution of polyacrylic acid (a reported average molecular weight of about 90,000, commercially available from Aldrich Chemical Company, Milwaukee, Wis., U.S.A.—contains about 84.4 grams polyacrylic acid and 253.2 grams water)

578.0 parts by weight of isopropanol

The carbon powder and isopropanol are combined by mixing in a conventional high shear colloid mill mixer (Ebenbach-type colloid mill) until the carbon is uniformly dispersed and the carbon particle size is smaller than 10 microns. At this point, the 25 weight percent solution of polyacrylic acid is added to the solution and mixed for approximately 15 minutes. The resulting mixture is pumped to the coating head and roll coated with a Meyer rod onto a sheet of aluminum foil (about 9 inches [ 22.86 cm] wide and about 0.0005 inches [0.00127 cm] thick). After application, the solution/foil are contacted with a Mylar wipe (about 0.002 inches [0.005 cm] thick by about 2 inches [5.0 cm] and by about 9 inches [22.86 cm] wide—the entire width of the aluminum foil). The wipe is flexibly engaged with the foil (i.e., the wipe merely contacts the foil) to redistribute the solution so as to provide for a substantially uniform coating. Evaporation of the solvents (i.e., water and isopropanol) via a conventional gas-fired oven provides for an electrically-conducting adhesion-promoter layer of about 6 microns in thickness or about 3×10$^{-4}$ grams per cm$^2$. The aluminum foil is then cut to about 8 inches (20.32 cm) wide by removing approximately 0.5 inch (1.27 cm) from either side by the use of a conventional slitter so as to remove any uneven edges.

In order to further remove the protic solvent from this layer, the foil is redried. In particular, the foil is wound up and a copper support placed through the roll's cavity. The roll is then hung overnight from the support in a vacuum oven maintained at about 130° C. Afterwards, the roll is removed. In order to avoid absorption of moisture from the atmosphere, the roll is preferably stored into a desiccator or other similar anhydrous environment to minimize atmospheric moisture content until the cathode paste is ready for application onto this roll.

The second preparation of this colloidal solution comprises mixing 25 lbs. (11.34 kg) of carbon powder (Shawinigan Black™—available from Chevron Chemical Company, San Ramon, Calif., U.S.A.) with 100 lbs. (45.35 kg) of a 25 weight percent solution of polyacrylic acid (average molecular weight of about 240,000, commercially available from BF Goodrich, Cleveland, Ohio, U.S.A., as Good-Rite K702—contains about 25 lbs. (11.34 kg) polyacrylic acid and 75 lbs. [34 kg] water) and with 18.5 lbs. (8.39 kg) of isopropanol. Stirring is done in a 30 gallon polyethylene drum with a gear-motor mixer (e.g., Lightin Labmaster Mixer, model XJ-43, available from Cole-Parmer Instruments Co., Niles, Ill., U.S.A.) at 720 rpm with two 5 inch (12.7 cm) diameter A310-type propellers mounted on a single shaft. This wets down the carbon and eliminates any further dust problem. The resulting weight of the mixture is 143.5 lbs. (65.09 kg) and contains some "lumps".

The mixture is then further mixed with an ink mill which consists of three steel rollers almost in contact with each other, turning at 275, 300, and 325 rpms respectively. This high shear operation allows particles that are sufficiently small to pass directly through the rollers. Those that do not pass through the rollers continue to mix in the ink mill until they are small enough to pass through these rollers. When the mixing is complete, the carbon powder is completely dispersed. A Hegman fineness of grind gauge (available from Paul N. Gardner Co., Pompano Beach, Fla., U.S.A.) indicates that the particles are 4–6 μm with the occasional 12.5 μm particles. The mixture can be stored for well over 1 month without the carbon settling out or reagglomerating.

When this composition is to be used to coat the current collector, an additional 55.5 lbs. (25.17 kg) of isopropanol is mixed into the composition working with 5 gallon (18,925 l) batches in a plastic pail using an air powered shaft mixer (Dayton model 42231 available from Granger Supply Co., San Jose, Calif., U.S.A.) with a 4 inch (10.16 cm) diameter Jiffy-Mixer brand impeller (such as an impeller available as Catalog No. G-04541–20 from Cole Parmer Instrument Co., Niles, Ill., U.S.A.). Then, it is gear pumped through a 25 μm cloth filter (e.g., So-Clean Filter Systems, American Felt and Filter Company, Newburgh, N.Y., U.S.A.) and Meyer-rod coated as described above.

B. The Cathode

The cathode is prepared from a cathodic paste which, in turn, is prepared from a cathode powder as follows:

i. Cathode Powder

The cathode powder is prepared by combining 90.44 weight percent $V_6O_{13}$ (prepared by heating ammonium metavanadate $[NH_4^+VO_3^-]$ at 450° C. for 16 hours under $N_2$ flow) and 9.56 weight percent of carbon (from Chevron Chemical Company, San Ramon, Calif., U.S.A. under the trade name of Shawinigan Black™). About 100 grams of the resulting mixture is placed into a grinding machine (Attritor Model S-1 purchased from Union Process, Akron, Ohio, U.S.A.) and ground for 30 minutes. Afterwards, the resulting mixture is dried at about 260° C. for 21 hours.

ii. Cathode Paste

A cathode paste is prepared by combining sufficient cathode powder to provide for a final product having 45 weight percent $V_6O_{13}$.

Specifically, 171.6 grams of a 4:1 weight ratio of propylene carbonate:triglyme are combined with 42.9 grams of polyethylene glycol diacrylate (molecular weight about 400 available as SR-344 from Sartomer Company, Inc., Exton, Pa., U.S.A.), and about 7.6 grams of ethoxylated trimethylolpropane triacrylate (TMPEOTA) (molecular weight about 450 available as SR-454 from Sartomer Company, Inc., Exton, Pennsylvania, U.S.A.) in a double planetary mixer (Ross #2 mixer available from Charles Ross & Sons, Company, Hauppag, N.Y., U.S.A.).

A propeller mixture is inserted into the double planetary mixer, and the resulting mixture is stirred at a 150 rpms until homogeneous. The resulting solution is then passed through sodiated 4A molecular sieves. The solution is then returned to double planetary mixer equipped with the propeller mixer and about 5 grams of polyethylene oxide (number average molecular weight about 600,000 available as Polyox WSR-205 from Union Carbide Chemicals and Plastics, Danbury, Conn., U.S.A.) is added to the solution vortex formed by the propeller by a mini-sieve such as a 25 mesh mini-sieve commercially available as Order No. 57333–965 from VWR Scientific, San Francisco, Calif., U.S.A.

The solution is then heated while stirring until the temperature of the solution reaches 65° C. At this point, stirring is continued until the solution is completely clear. The propeller blade is removed, and the cathode powder prepared as above is then added as well as an additional 28.71 grams of unground carbon (from Chevron Chemical Company, San Ramon, Calif., U.S.A. under the trade name of Shawinigan Black™). The resulting mixture is mixed at a rate of 7.5 cycles per second for 30 minutes in the double planetary mixer. During this mixing the temperature is slowly increased to a maximum of 73° C. At this point, the mixing is reduced to 1 cycle per second and the mixture slowly cooled to 40° C. to 48° C. (e.g. about 45° C.). The resulting cathode paste is maintained at this temperature until just prior to application onto the current collector.

The resulting cathode paste has the following approximate weight percent of components:

| | |
|---|---|
| $V_6O_{13}$ | 45 weight percent |
| Carbon | 10 weight percent |
| 4:1 propylene carbonate/triglyme | 34 weight percent |
| polyethylene oxide | 1 weight percent |
| polyethylene glycol diacrylate | 8.5 weight percent |
| ethoxylated trimethylolpropane triacrylate | 1.5 weight percent |

In an alternative embodiment, the requisite amounts of all of the solid components are added directly to combined liquid components. In this regard, mixing speeds can be adjusted to account for the amount of the material mixed and size of vessel used to prepare the cathode paste. Such adjustments are well known to the skilled artisan.

In order to enhance the coatability of the cathode paste onto the current collector, it may be desirable to heat the paste to a temperature of from about 60° C. to about 130° C., and more preferably, from about 80° C. to about 90° C. and for a period of time of from about 0.1 to about 2 hours, more preferably, from about 0.1 to 1 hour and even more preferably from about 0.2 to 1 hour. A particularly preferred combination is to heat the paste at from about 80° C. to about 90° C. for about 0.33 to about 0.5 hour.

During this heating step, there is no need to stir or mix the paste although such stirring or mixing may be conducted during this step. However, the only requirement is that the composition be heated during this period. In this regard, the composition to be heated has a volume to surface area ratio such that the entire mass is heated during the heating step.

A further description of this heating step is set forth in U.S. Patent application Ser. No. 07/968,203 filed Oct. 29, 1992, which application is incorporated herein by reference in its entirety.

The so-prepared cathode paste is then placed onto the adhesion layer of the current collector described above by extrusion at a temperature of from about 45° C. to about 48° C. A Mylar cover sheet is then placed over the paste, and the paste is spread to thickness of about 90 microns (μm) with a conventional plate and roller system and is cured by continuously passing the sheet through an electron beam apparatus (Electrocurtain, Energy Science Inc., Woburn, Mass., U.S.A.) at a voltage of about 175 kV and a current of about 1.0 mA and at a rate of about 1 cm/sec. After curing, the Mylar sheet is removed to provide for a solid cathode laminated to the aluminum current collector described above.

C. Electrolyte 56.51 grams of propylene carbonate, 14.13 grams of triglyme, and 17.56 grams of the compound prepared as per Example 1 above are combined at room temperature until homogeneous. The resulting solution is passed through a column of 4A sodiated molecular sieves to remove water and then mixed at room temperature until homogeneous.

At this point, 2.57 grams of polyethylene oxide film forming agent having a number average molecular weight of about 600,000 (available as Polyox WSR-205 from Union Carbide Chemicals and Plastics, Danbury, Conn., U.S.A.) is added to the solution and then dispersed while stirring with a magnetic stirrer over a period of about 120 minutes. After dispersion, the solution is heated to between 60° C. and 65° C. with stirring until the film forming agent dissolved. The solution is cooled to a temperature of between 45° C. and 48° C., a thermocouple is placed at the edge of the vortex created by the magnetic stirrer to monitor solution temperature, and then 9.24 grams of $LiPF_6$ is added to the solution over a 120 minute period while thoroughly mixing to ensure a substantially uniform temperature profile throughout the solution. Cooling is applied as necessary to maintain the temperature of the solution between 45° C. and 48° C.

In one embodiment, the polyethylene oxide film forming agent is added to the solution via a mini-sieve such as a 25 mesh mini-sieve commercially available as Order No. 57333–965 from VWR Scientific, San Francisco, Calif., U.S.A.

The resulting solution contains the following:

| Component | Amount | Weight Percent[a] |
|---|---|---|
| Propylene Carbonate | 56.51 g | 56.51 |
| Triglyme | 14.13 g | 14.13 |
| Compound of Example 1 | 17.56 g | 17.56 |
| $LiPF_6$ | 9.24 g | 9.24 |
| PEO Film Forming Agent | 2.57 g | 2.57 |
| Total | 100 g | 100 |

[a] = weight percent based on the total weight of the electrolyte solution (100 g)

This solution is then degassed to provide for an electrolyte solution wherein little, if any, of the $LiPF_6$ salt decomposes.

Optionally, solutions produced as above and which contain the compound of Example 1, the polyalkylene oxide film forming agent, the electrolyte solvent and the $LiPF_6$ salt are filtered to remove any solid particles or gels remaining in the solution. One suitable filter device is a sintered stainless steel screen having a pore size between 1 and 50 μm at 100% efficiency.

Alternatively, the electrolyte solution can be prepared in the following manner. Specifically, in this example, the mixing procedure is conducted using the following weight percent of components:

| | |
|---|---|
| Propylene Carbonate | 52.472 weight percent |
| Triglyme | 13.099 weight percent |
| Compound of Example 1 | 20.379 weight percent |
| $LiPF_6$ | 10.720 weight percent |
| PEO Film Forming Agent[b] | 3.340 weight percent |

[b] polyethylene oxide film forming agent having a number average molecular weight of about 600,000 (available as Polyox WSR-205 from Union Carbide Chemicals and Plastics, Danbury, Connecticut, U.S.A.)

The mixing procedure employs the following steps:

1. Check the moisture level of the compound of Example 1. If the moisture level is less than 100 ppm water, proceed to step 2. If not, then first dissolve this compound at room temperature, <30° C., in the propylene carbonate and triglyme mixture and dry the solution over sodiated 4A molecular sieves (Grade 514, 8–12 Mesh from Schoofs Inc., Moraga, Calif., U.S.A.) and then proceed to step 4.

2. Dry the propylene carbonate and triglyme over sodiated 4A molecular sieves (Grade 514, 8–12 Mesh from Schoofs Inc., Moraga, Calif., U.S.A.).

3. At room temperature, <30° C., add the compound of Example 1 to the solvent prepared in step 2. Stir at 300 rpm until the compound is completely dissolved. The solution should be clear and colorless.

4. Dry and then sift the polyethylene oxide film forming agent through a 25 mesh mini-sieve commercially available as Order No. 57333–965 from VWR Scientific, San Francisco, Calif., U.S.A. While stirring at 300 rpm, add the dried and pre-sifted polyethylene oxide film forming agent slowly to the solution. The polyethylene oxide film forming agent should be sifted into the center of the vortex formed by the stirring means over a 30 minute period. Addition of the polyethylene oxide film forming agent should be dispersive, and, during addition, the temperature should be maintained at room temperature (<30° C.).

5. After final addition of the polyethylene oxide film forming agent, stir an additional 30 minutes to ensure that the film forming agent is substantially dispersed.

6. Heat the mixture to 68° C. to 75° C. and stir until the film forming agent has melted and the solution has become transparent to light yellow in color. Optionally, in this step, the mixture is heated to 65° C. to 68° C.

7. Cool the solution produced in step 6, and when the temperature of the solution reaches 40° C., add the $LiPF_6$ salt very slowly making sure that the maximum temperature does not exceed 55° C.

8. After the final addition of the $LiPF_6$ salt, stir for an additional 30 minutes, degas, and let sit overnight and cool.

9. Filter the solution through a sintered stainless steel screen having a pore size between 1 and 50 μm at 100% efficiency.

At all times, the temperature of the solution should be monitored with a thermocouple which should be placed in the vortex formed by the mixer.

Afterwards, the electrolyte mixture is then coated by a conventional knife blade to a thickness of about 50 μm onto the surface of the cathode sheet prepared as above (on the side opposite that of the current collector) but without the Mylar covering. The electrolyte is then cured by continuously passing the sheet through an electron beam apparatus (Electrocurtain, Energy Science Inc., Woburn, Mass., U.S.A.) at a voltage of about 175 kV and a current of about 1.0 mA and at a conveyor speed setting of 50 which provides for a conveyor speed of about 1 cm/sec. After curing, a composite is recovered which contains a solid electrolyte laminated to a solid cathode.

D. Anode

The anode comprises a sheet of lithium foil (about 76 μm thick) which is commercially available from FMC Corporation Lithium Division, Bessemer City, N.C., U.S.A.

E. The Solid Electrolytic Cell

A sheet comprising a solid electrolytic cell is prepared by laminating the lithium foil anode to the surface of the electrolyte in the sheet produced in step C. above. Lamination is accomplished by minimal pressure.

By following the procedure set forth in Examples 1 and 2 above, other vinyl sulfonate derivatives can be substituted in place of

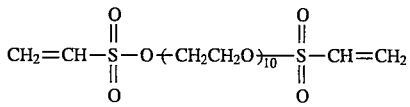

Such other vinyl sulfonates include those of formulas B, C, D and E above. Specific examples include $ZOC_6H_{12}OZ$,

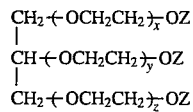

where x+y+z equals 26, where Z is in all cases equal to

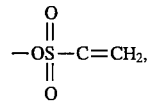

and the like.

What is claimed is:

1. A compound selected from the group consisting of the compounds set forth in formulas A, B, C, D and E below:

i

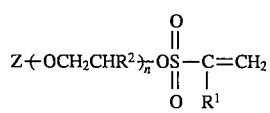

where $R^1$ is selected from the group consisting of hydrogen and alkyl of from 1 to 6 carbon atoms; $R^2$ is selected from the group consisting of hydrogen and an alkyl group of from 1 to 3 carbon atoms; Z is selected from the group consisting of a hydrocarbyl group of from 1 to 30 carbon atoms and a compatible ethylenically unsaturated moiety of from 2 to 6 carbon atoms; and n is an integer from about 2 to 50;

ii

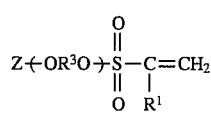

wherein $R^3$ is an alkylene group of from 2 to 10 carbon atoms, $R^1$ is selected from the group consisting of hydrogen and alkyl of from 1 to 6 carbon atoms; and Z is selected from the group consisting of a hydrocarbyl group of from 1 to 30 carbon atoms and a compatible ethylenically unsaturated moiety of from 2 to 6 carbon atoms;

iii

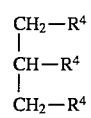

wherein each $R^4$ is independently selected from the group consisting of $-(OCH_2CHR^2)-_mOZ'$ where $R^2$ is hydrogen or an alkyl group of from 1 to 3 carbon atoms, Z' is a compatible ethylenic unsaturated moiety of from 2 to 6 carbon atoms, and m is an integer from 0 to 50, with the proviso that at least one Z' is

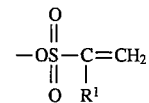

wherein $R^1$ is selected from the group consisting of hydrogen and alkyl of from 1 to 6 carbon atoms;

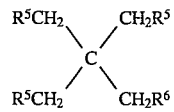

wherein $R^1$ is selected from the group consisting of consisting of $-(OCH_2CHR^2)-_mOZ'$ where $R^2$ is hydrogen or an alkyl group of from 1 to 3 carbon atoms, Z' is a compatible ethylenic unsaturated moiety of from 2 to 6 carbon atoms, and m is an integer from 0 to 50, and $R^6$ is selected from the group consisting of hydrogen, alkyl of from 1 to 3 carbon atoms, and $-(OCH_2CHR^2)-_mOZ'$ where $R^2$, Z' and m are as defined above with the proviso that at least one Z' is

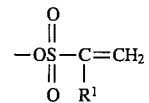

wherein $R^1$ is selected from the group consisting of hydrogen and alkyl of from 1 to 6 carbon atoms; and v

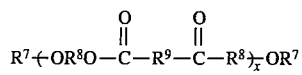

wherein x is an integer of from 1 to 50; each $R^8$ and $R^9$ is independently an alkylene group of from 2 to 10 carbon atoms; each $R^7$ is independently selected from the group consisting of a hydrocarbyl group of from 1 to 30 carbon atoms and $-(CH_2CHR^2O)-_mZ'$ where $R^2$ is selected from the group consisting of hydrogen and alkyl of from to 3 carbon atoms, m is an integer from 0 to 50, and Z' is a compatible ethylenic unsaturated moiety of from to 6 carbon atoms, with the proviso that at least one of $R^7$ is:

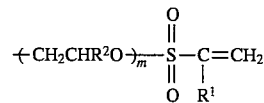

wherein $R^1$ is selected from the group consisting of hydrogen and alkyl of from 1 to 6 carbon atoms; and $R^2$ and m are as defined above.

2. The compound according to claim 1 wherein said compound is of formula A and further wherein Z is

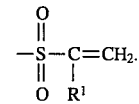

3. The compound according to claim 1 wherein said compound is of formula B and further wherein Z is

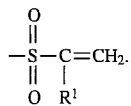

4. The compound according to claim 1 wherein said compound is of formula C and each of $R^4$ is

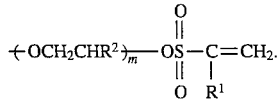

5. The compound according to claim 1 wherein said compound is of the formula D and each of $R^5$ is

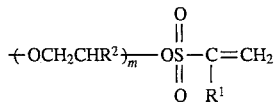

and further wherein $R^6$ is hydrogen or

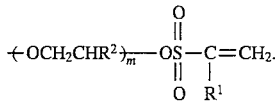

6. The compound according to claim 1 wherein said compound is of the formula E and each of $R^7$ is

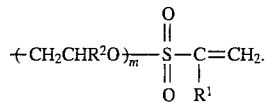

7. The compound according to any one of claims 1–6 wherein $R^1$ is hydrogen or methyl.

8. The compound according to claim 7 wherein $R^2$ is hydrogen or methyl, m is an integer from 0 to about 30, and n is an integer from 3 to about 30.

9. A single-phase, solid, solvent-containing electrolyte which comprises:

a solid polymeric matrix;

an inorganic ion salt; and an electrolyte solvent; wherein said solid polymeric matrix is obtained by polymerizing an organic monomer of formulas A–E as defined in claim 1.

10. The single-phase, solid, solvent-containing electrolyte according to claim 9 wherein said solid polymeric matrix is obtained by polymerizing an organic monomer of formula A and further wherein Z is

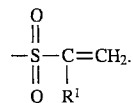

11. The single-phase, solid, solvent-containing electrolyte according to claim 9 wherein said solid polymeric matrix is obtained by polymerizing an organic monomer of formula B and further wherein Z is

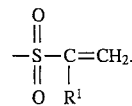

12. The single-phase, solid, solvent-containing electrolyte according to claim 9 wherein said solid polymeric matrix is obtained by polymerizing an organic monomer of formula C and further wherein each of $R^4$ is

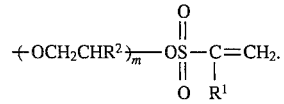

13. The single-phase, solid, solvent-containing electrolyte according to claim 9 wherein said solid polymeric matrix is obtained by polymerizing an organic monomer of formula D and further wherein each of $R^5$ is

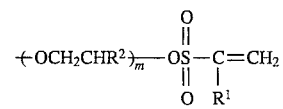

and further wherein $R^6$ is hydrogen or

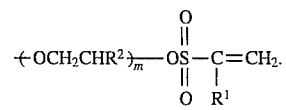

14. The single-phase, solid, solvent-containing electrolyte according to claim 9 wherein said solid polymeric matrix is obtained by polymerizing an organic monomer of formula E and further wherein each of $R^7$ is

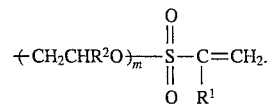

15. The single-phase, solid, solvent-containing electrolyte according to any one of claim 9 through 14 wherein $R^1$ is hydrogen or methyl.

16. The single-phase, solid, solvent-containing electrolyte according to claim 15 wherein $R^2$ is hydrogen or methyl, m is an integer from 0 to about 30, and n is an integer from 3 to about 30.

17. An electrolytic cell which comprises:

an anode comprising a compatible anodic material;

a cathode comprising a compatible cathodic material; and interposed therebetween a single-phase, solid, solvent-containing electrolyte which comprises:

a solid polymeric matrix;

an inorganic ion salt; and an electrolyte solvent; wherein said solid polymeric matrix is obtained by polymerizing an organic monomer of formulas A–E as defined in claim 1.

18. The electrolytic cell according to claim 17 wherein said electrolyte's solid polymeric matrix is obtained by polymerizing an organic monomer of formula A and further wherein Z is

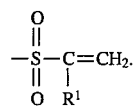

19. The electrolytic cell according to claim 17 wherein said electrolyte's solid polymeric matrix is obtained by polymerizing an organic monomer of formula B and further wherein Z is

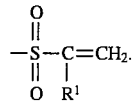

20. The electrolytic cell according to claim 17 wherein said electrolyte's solid polymeric matrix is obtained by polymerizing an organic monomer of formula C and further wherein each of $R^4$ is

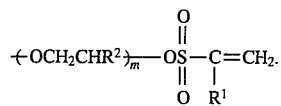

21. The electrolytic cell according to claim 17 wherein said electrolyte's solid polymeric matrix is obtained by polymerizing an organic monomer of formula D and further wherein each of $R^5$ is

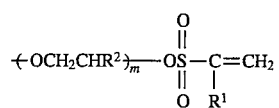

and further wherein $R^6$ is hydrogen or

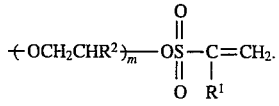

22. The electrolytic cell according to claim 17 wherein said electrolyte's solid polymeric matrix is obtained by polymerizing an organic monomer of formula E and further wherein each of $R^7$ is

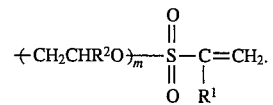

23. The electrolytic cell according to any one of claims 17 through 22 wherein $R^1$ is hydrogen or methyl.

24. The electrolytic cell according to claim 23 wherein $R^2$ is hydrogen or methyl, m is an integer from 0 to about 30, and n is an integer from 3 to about 30.

* * * * *